(12) United States Patent
Thuo et al.

(10) Patent No.: US 10,293,325 B2
(45) Date of Patent: May 21, 2019

(54) CORE-SHELL MULTI-LAYER PARTICLES

(71) Applicant: UNIVERSITY OF MASSACHUSETTS, Boston, MA (US)

(72) Inventors: Martin Thuo, Ames, IA (US); Ian Tevis, Brighton, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 257 days.

(21) Appl. No.: 15/103,648

(22) PCT Filed: Dec. 11, 2014

(86) PCT No.: PCT/US2014/069802
§ 371 (c)(1),
(2) Date: Jun. 10, 2016

(87) PCT Pub. No.: WO2015/089309
PCT Pub. Date: Jun. 18, 2015

(65) Prior Publication Data
US 2016/0317992 A1    Nov. 3, 2016

Related U.S. Application Data

(60) Provisional application No. 61/914,765, filed on Dec. 11, 2013.

(51) Int. Cl.
*B01J 13/14* (2006.01)
*B01J 13/04* (2006.01)
(Continued)

(52) U.S. Cl.
CPC .......... *B01J 13/04* (2013.01); *A61K 49/0002* (2013.01); *B01J 13/14* (2013.01); *B01J 13/22* (2013.01);
(Continued)

(58) Field of Classification Search
CPC .............................. C09D 5/004; B01J 13/0047
See application file for complete search history.

(56) References Cited

U.S. PATENT DOCUMENTS 3,788,955 A    1/1974   Crites et al.
2011/0259244 A1  10/2011  Herbig et al.
(Continued)

FOREIGN PATENT DOCUMENTS

EP    2463231 A1     6/2012
WO   2013178802 A2   12/2013

OTHER PUBLICATIONS

International Search Report and Written Opinion of the International Searching Authority for Application PCT/US14/69802 dated Feb. 26, 2015.
(Continued)

*Primary Examiner* — Kara B Boyle
(74) *Attorney, Agent, or Firm* — Lando & Anastasi, LLP

(57) ABSTRACT

According to various aspects and embodiments, core-shell particles and methods of making the same are disclosed. The core-shell particles may include a liquid metal core, at least one layer of inorganic material surrounding the liquid metal core, and at least one layer of organic material attached to the at least one layer of inorganic material.

11 Claims, 8 Drawing Sheets

(51) Int. Cl.
  B82Y 40/00    (2011.01)
  B01J 13/22    (2006.01)
  A61K 49/00    (2006.01)
  B23K 35/02    (2006.01)
  B23K 35/26    (2006.01)
  C09D 5/33     (2006.01)
  C09D 5/24     (2006.01)
  C09D 11/037   (2014.01)
  C09D 11/52    (2014.01)
  B82Y 30/00    (2011.01)

(52) U.S. Cl.
  CPC .......... *B23K 35/0244* (2013.01); *B23K 35/26* (2013.01); *B82Y 40/00* (2013.01); *C09D 5/004* (2013.01); *C09D 5/24* (2013.01); *C09D 11/037* (2013.01); *C09D 11/52* (2013.01); *B82Y 30/00* (2013.01)

(56) References Cited

U.S. PATENT DOCUMENTS

2012/0039824 A1    2/2012   Archer et al.
2013/0244037 A1*   9/2013   Hohman ............... B82Y 30/00
                                                   428/402.2

OTHER PUBLICATIONS

Fracasso et al., "Evidence for Quantum Interference in SAMs of Arylethynylene Thiolates in Tunneling Junctions with Eutectic GaIn (EGaIn) Top-Contacts" Journal of the American Chemical Society. May 11, 2011. dx.doi.org/10.1021/ja202471m. p. 9556, col. 1, paragraph 1; p. 9557, figure 1.

* cited by examiner

CORE-SHELL MULTI-LAYER PARTICLES

CROSS-REFERENCE TO RELATED APPLICATIONS

This application is a U.S. national phase application and claims the benefit of priority under 35 U.S.C. § 371 of PCT/US2014/069802, filed Dec. 11, 2014, which in turn claims priority under 35 U.S.C. § 119(e) to U.S. Provisional Patent Application Ser. No. 61/914,765, titled "CORE-SHELL MULTI-LAYER PARTICLES," filed Dec. 11, 2013, which is hereby incorporated herein by reference in its entirety for all purposes.

BACKGROUND

Technical Field

The technical field relates generally to core-shell multi-layered mico- and nano-sized particles derived from low-temperature melting point metals and metal alloys using a top-down process that includes fluidic shearing and surface functionalization.

Background Discussion

Small two-layer particles having a liquid metal core and a hard shell are currently produced using a variety of techniques. For example, liquid metal marbles and liquid metal/metal oxide frameworks may be made by coating liquid metal droplets with metal oxides, Teflon™, silica, or carbon nanotube films. Liquid metal nanoparticles may also be made by dividing a macroscopic drop of liquid metal using ultrasonic scissioning in the presence of a stabilizer, and microparticles of metal and metal alloys have been created using a droplet emulsion technique (DET) by shearing a molten metal in the presence of a carrier fluid.

SUMMARY

Aspects and embodiments are directed to a core-shell particle comprising a liquid metal core, at least one layer of inorganic material surrounding the liquid metal core, and at least one layer of organic material attached to the at least one layer of inorganic material.

In accordance with one or more aspects, a core-shell particle may comprise a liquid metal core, at least one layer of inorganic material surrounding the liquid metal core, and at least one layer of organic material attached to the at least one layer of inorganic material.

In some aspects, the liquid metal core may be a metal alloy. The liquid metal core may have a melting point temperature less than or equal to about 40° C. In some specific aspects, the liquid metal core comprises gallium. The at least one layer of organic material may be derived from a carboxylic acid. In some aspects, the carboxylic acid is acetic acid. In various aspects, the core-shell particle may have a viscosity in a range of from about 0.89 cP to about 1.64 cP. The core-shell particle may be at least one of a micro- and nano-sized particle.

In accordance with one or more aspects, a method for producing a core-shell particle may comprise combining a liquid metal, at least one carrier fluid, and at least one organic material in the presence of an oxidizer to form a solution, applying mixing forces to the solution to produce a suspension comprising a plurality of core-shell particles, and removing at least a portion of the plurality of core-shell particles from the suspension.

In some aspects, the mixing forces may be at least one of shear forces, cavitation forces, milling forces, ultrasonic forces, laser ablation forces, atomization forces, and compressive forces, applied by at least one device comprising high pressure homogenizers, jet stream devices, rotar-stator colloid mills, ball mills, high shear mixers, ultrasonic devices, mechanical alloying devices, laser devices, and atomization devices. The mixing force may be a shear force that creates a shear rate in a range of from about 600 $s^{-1}$ to about 3100 $s^{-1}$. The mixing forces may be applied for a period of time sufficient to produce a plurality of core-shell particles comprising at least one of micro- and nano-sized particles. In some aspects, the carrier fluid functions as the oxidizer. Combining the liquid metal, the at least one carrier fluid, and the at least one organic material may be performed in the presence of air. The carrier fluid may be at least one of water and hydrogen peroxide. The at least one organic material may be a carboxylic acid. In some specific aspects, the liquid metal comprises gallium. In some aspects, the polydispersity index of the suspension is in a range of from about 1.1 to about 4.0. The at least one carrier fluid may be a first carrier fluid and the at least one organic material may be a first organic material. The method may further comprise etching at least one core-shell particle and reacting the etched at least one core-shell particle with a second carrier fluid and a second organic material, wherein at least one of the second carrier fluid and the second organic material are different than the first carrier fluid and first organic material, respectively. In some aspects, the method may further comprise reacting at least one core-shell particle with at least one reactant to create at least one of a cross-linked or polymerized layer on the outer surface of the at least one core-shell particle.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments," "some examples," "an alternate embodiment," "various embodiments," "one embodiment," "at least one embodiment," "this and other embodiments" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Figure 1:
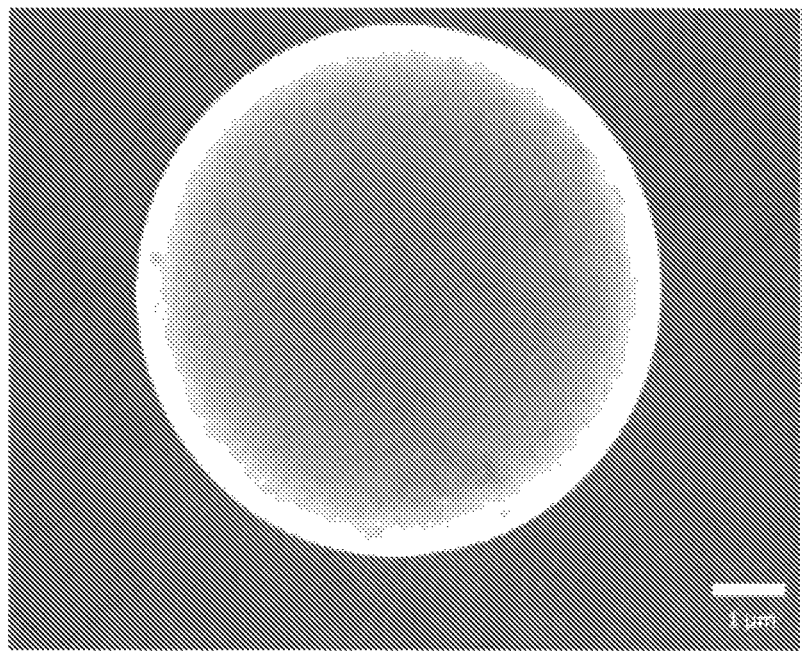
FIG. 1 is a scanning electron microscope (SEM) image of a galinstan core-shell particle in accordance with one or more aspects of the invention.

By way of introduction, aspects of this disclosure relate to scalable systems and methods for producing core-shell particles derived from low-temperature melting point liquid metals by applying mixing forces and sequential surface reactions. The core-shell particles may be multi-layered and include at least one layer of inorganic material and at least one layer of inorganic material. The core-shell particles may be micro- or nano-sized and may be generally described as malleable in their overall physical consistency.

The core-shell particles described herein may be prepared using a method of shearing liquid metals into complex particles. The disclosed approach generally combines both mechanical and chemical principles to create multi-layer core-shell micro- and nano-sized particles. Further, self-assembly principles may be applied post-synthesis to create unique assembled structures. Thus, the low-temperature melting point metals and metal alloys are effectively broken up into smaller sized particles under fluid flow with concomitant surface oxidation and functionalization. The methods and systems disclosed herein may provide one or more advantages over other currently available methods and systems. For example, the methods disclosed here may be used to create micro- and nano-sized particles that are tunable, green (eco-friendly), and inexpensive.

The aspects disclosed herein in accordance with the present invention, are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

Core-Shell Particles

In accordance with one or more embodiments, core-shell particles are provided. The core-shell particles may comprise a liquid metal core. As used herein, the term "liquid metal" refers to at least one metal or metal alloy having a melting point at a temperature less than or equal to, for example, about 40° C., about 35° C., about 30° C., about 25° C., about 20° C., about 15° C. According to some embodiments, the liquid metal core comprises gallium, which has a melting point of about 30° C. Many metallic alloys are also known to be liquid in these temperature ranges. For example, many alloys of gallium (Ga) that include at least one of indium (In), tin (Sn), and/or zinc (Zn) are also known to be liquid in these temperature ranges. For instance, a gallium alloy commercially known as galinstan, which typically has about 68.5% Ga, about 21.5% In, and about 10% Sn has a melting point of about −19° C. According to other embodiments, the liquid metal core comprises gallium-indium, including eutectic gallium-indium (EGaIn), which typically contains about 75% gallium and 24.5% indium by weight and has a melting point of about 15.7° C. Non-limiting examples of other low-temperature melting point metals and metal alloys include one or more of bismuth (Bi), lead (Pb), cadmium (Cd), mercury (Hg), thallium (Tl), and sodium-potassium (NaK). The liquid metal may be any metal with a melting point at a temperature that is below the temperature of the desired application of the core-shell particle and is suitable for performing the requisite functions of the desired application. Further, the liquid metal core may be reversibly converted from liquid to solid and/or from soft core to hard core through temperature variation. The liquid metal may also be selected depending on a desired application. For instance, in applications where non-toxicity to humans is important, the liquid metal may be Ga or EGaIn, or any other metal that is non-toxic.

In accordance with at least one embodiment, the liquid metal core may be surrounded by at least one layer of inorganic material. As used herein, the term "inorganic material" refers to non-carbon based materials. According to some embodiments, the inorganic material is capable of reacting with metal, including the liquid metals discussed above. Non-limiting examples of inorganic materials include oxides. For example, the at least one layer of inorganic material may be a metal oxide, a metal sub-oxide, or a combination of both. According to various embodiments, the inorganic material may be produced using any suitable oxidizer with the desired reactivity, non-limiting examples of which include water, oxygen, and hydrogen peroxide.

In accordance with other embodiments, and as discussed further below, the liquid metal may react with the inorganic material to form an oxynitride. Oxynitrides may be useful for several applications, including catalytic applications. Thus, the inorganic material may be any suitable material that reacts with the liquid metal to form a layer of metal oxynitride.

According to certain aspects, the at least one layer of inorganic material is a self-passivating layer, such as an oxide, that is formed from the reaction of the liquid metal with an oxidizer such as air or water. In accordance with at least one embodiment, the at least one layer of inorganic material is less than 1 nm in thickness. According to some embodiments, the at least one layer of inorganic material is several atoms thick. In certain instances, the at least one layer of oxide may have a thickness of at least about 0.7 nm, and may be made thicker by subjecting the liquid metal core to further oxidation conditions, as discussed further below.

In accordance with some embodiments, at least one layer of organic material is attached to the at least one layer of inorganic material. As used herein, the term "organic material" refers to a carbon-based material. According to certain embodiments, the organic material is capable of attaching to the inorganic material discussed above. In some embodiments, the organic material is a carboxylic acid, or derived from a carboxylic acid. For example, carboxylic acids are known to bind to metal oxide surfaces. According to some embodiments, acetic acid binds to the metal oxide to form at least one layer of acetate bound on the oxide. Non-limiting examples of carboxylic acids include saturated aliphatic carboxylic acids having one to 20 carbon atoms such as formic acid, acetic acid, propanoic acid, butyric acid, hexanoic acid, heptanoic acid, octanoic acid, decanoic acid, and higher aliphatic acids such as hexadecanoic acid and octadecanoic acid. Shorter acids, such as acetic acid, do not crosslink with themselves, but longer acids, such as octanoic acid, may crosslink with itself due to the longer chain length. The carboxylic acid may be of any length or shape, provided that the carboxylic acid is capable of accessing the surface of the inorganic material. Other examples of carboxylic acids include unsaturated aliphatic carboxylic acids, alicyclic carboxylic acids, aromatic carboxylic acids, and polycarboxylic acids. In accordance with some embodiments, the carboxylic acids may include functional substituents, such as halogen, hydroxyl, nitro, alkyl, alkoxy, aldehyde, ester, and/or cyano groups. For example, one or more additional functional groups may be included in a longer chain acid, including hydrogen bonding groups such as amides. In certain instances, these functional groups may also be cross-linked via hydrogen bonding. According to another aspect, other groups, such as carbon-carbon double bonds, may be included and then chemically cross-linked after synthesis of the core-shell particle. Thus, the core-shell particles may include one or more layers of organic material(s) that are cross-linked. The organic material may be any material that is capable of bonding or otherwise attaching to the inorganic material and contributes toward the functionality of the core-shell particle as disclosed herein.

According to at least one embodiment, the at least one layer of organic material attaches to the at least one layer of inorganic material to form ligands that may be tightly packed in their physical arrangement, disperse in their physical arrangement, or some intermediate arrangement in between. For example, as discussed above, shorter acids such as acetic acid form ligands that are disperse in their physical arrangement, whereas longer-chain acids, such as octanoic acid, are capable of forming ligands that form more tightly packed arrangements. In certain instances, the tightly packed ligands may form one or more monolayers. According to some embodiments, the ligands may include a polymerizable functional group such as an ethylene group that may be polymerized to form the organic layer. For instance, the polymerizable functional group may be cross-linked or polymerized with one or more additional reactants to grow the layer of organic material. According to a further aspect, the at least one layer of organic material may be further surrounded by one or more additional layers of functional material. For example, polymers that contain hydrophilic groups such as polyethylene glycol may "wrap" the core-shell particle without binding, such as through the use of non-covalent interactions, to the layer of organic material. These types of materials may also be suitable for "wrapping" the at least one layer of inorganic material using the same non-covalent interactions, such as dispersion forces and weak dipole-dipole interactions.

Figure 2:
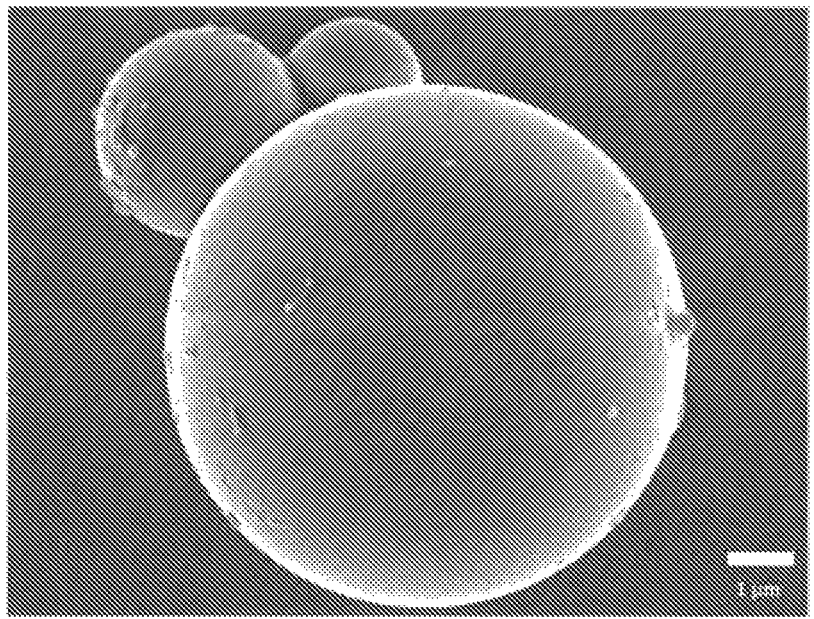
FIG. 2 is a SEM image of several gallium core-shell particles in accordance with one or more aspects of the invention.

In accordance with at least one embodiment, the core-shell particle is a nanoparticle. As used herein, the terms "nanoparticle" and "nano-sized particle" are used interchangeably and refer to a particle having a diameter that is less than 100 nanometers (0.1 micron). According to another embodiment, the core-shell particle is a microparticle. As used herein, the terms "microparticle" and "micro-sized particle" are used interchangeably and refer to a particle having an average diameter of from about 0.1 microns to about 100 microns. For example, FIGS. 1 and 2 show SEM images of core-shell particles made from galinstan and Ga microparticles, respectively.

Figure 3:
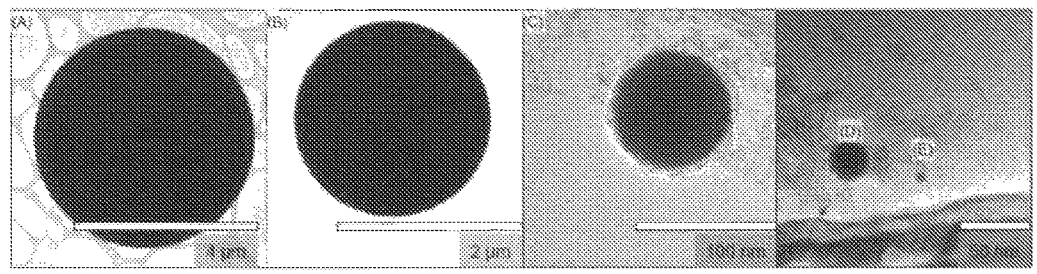
FIG. 3 shows a series of transmission electron microscope (TEM) images of several EGaIn particles of various sizes in accordance with one or more aspects of the invention.
Figure 4:
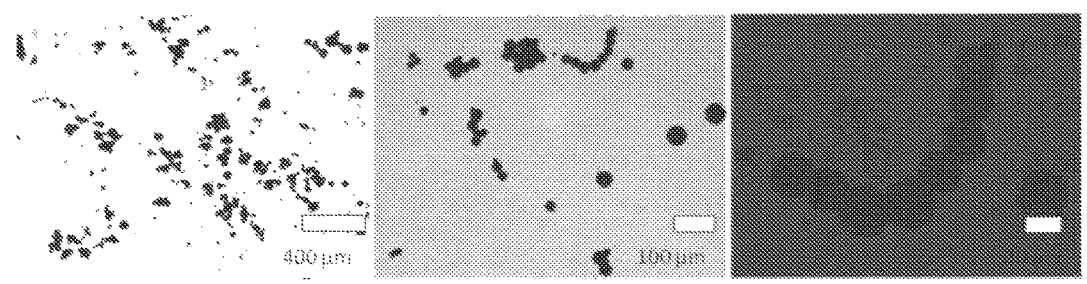
FIG. 4 shows a series of images of several eutectic gallium indium (EGaIn) core-shell particles imaged by light microscopy at various magnification levels in accordance with one or more aspects of the invention.
Figure 5:
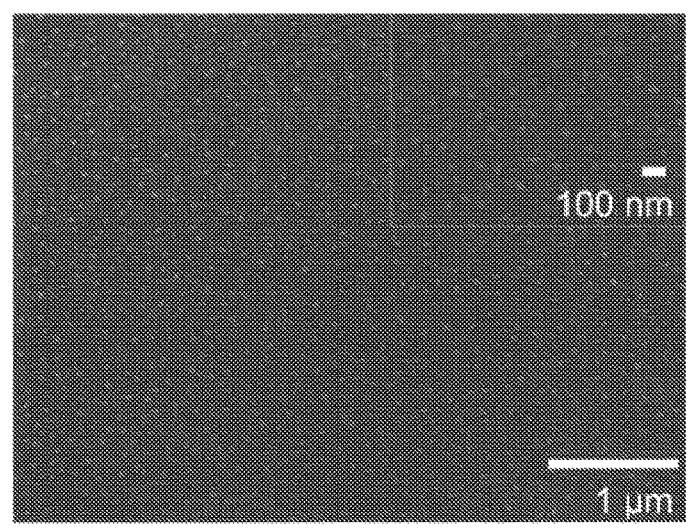
FIG. 5 is a SEM micrograph showing an image of a large field of nano-sized core-shell particles in accordance with one or more aspects of the invention.

In accordance with some embodiments, the core-shell particle has a diameter in a range of from about 6.4 nm to about 10 microns, although smaller and larger particles are within the scope of this disclosure. The size of the core-shell particle may be controlled through various processing methods, as discussed further below. FIGS. 3-5 show images of core-shell particles of various sizes. For example, FIG. 3 is a series of TEM images showing EGaIn particles of various sizes, from microscale (A), down to the single-digit nanoscale (E). FIG. 4 shows a series of EGaIn core-shell particles imaged by light microscopy at a magnification of (A) 40×, (B) 100×, and (C) 400×, and FIG. 5 (and FIG. 7H) is a SEM micrograph image of a large field of nanoparticles.

According to certain embodiments, the core-shell particle is malleable. As used herein, the term "malleable" as it applies to the core-shell particle means that the particle has a degree of deformability and/or pliability that allows the particle to be shaped or formed. According to at least one embodiment, the particle may have a viscosity of about 1.53 cP. For example, according to certain aspects, the core-shell particle may be characterized as being more viscous than water (0.89 cP) and less viscous than kerosene (1.64 cP), and therefore may have a viscosity in a range of from about 0.89 cP to about 1.64 cP. According to a further aspect, the core-shell particle may be described as being deformable. One or more of the liquid metal core, the at least one layer of inorganic material, and the at least one layer of organic material may contribute to the general deformability and/or malleable nature of the overall particle. For example, the layer of inorganic material may tightly adhere to the metal and possess an intermediate level of hardness and yet still having a malleable consistency. In addition, the layer of organic material may be "softer" than the inorganic material and be characterized as flexible.

In accordance with certain aspects, the core-shell particles may be self-repairing. For example, if the inorganic layer such as an oxide is punctured, scratched, or otherwise breached, then it may quickly reform and thereby "re-seal" the particle. In certain instances, this self-repairing characteristic may be due to the fact that the particle is in the presence of oxygen, which, as discussed above, readily bonds with the liquid metal core to form a metal oxide.

According to some aspects, one or more physical properties of the core-shell particle may be controlled through the choice of materials used to construct the particle. For example, a magnetic metal or metal alloy may be used for the liquid metal core, which may render the resulting core-shell particle magnetic.

Process

In accordance with one or more embodiments, a method for producing a core-shell particle is provided. The method may comprise combining a liquid metal, at least one carrier fluid, and at least one organic material in the presence of an oxidizer to form a solution. The liquid metal may be provided as discussed and described above, and according to certain aspects, the liquid metal remains in liquid form in the presence of the carrier fluid. According to some embodiments, the at least one carrier fluid serves as a medium for distributing the liquid metal. In accordance with various embodiments, the carrier fluid is a Newtonian fluid, such as water. Newtonian fluids undergo strain rates that are proportional to the applied shear stress, which, according to some aspects, may enhance the predictability of the particle's size and shape. According to alternative embodiments, a non-Newtonian fluid may be used for preparing the particles.

In certain embodiments, the at least one carrier fluid reacts with the liquid metal to form the at least one layer of inorganic material, as discussed above. For example, according to some embodiments, the at least one carrier fluid is an oxidizer. As used herein, the term "oxidizer" refers to a substance that yields oxygen that is available to bind with the liquid metal. Non-limiting examples of oxidizers include oxygen, air, ozone, hydrogen peroxide, and water. For example, gallium oxide is formed from the reaction of gallium and oxygen according to the formula below and as shown in the schematic of FIG. 6C:

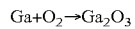

Figure 6:
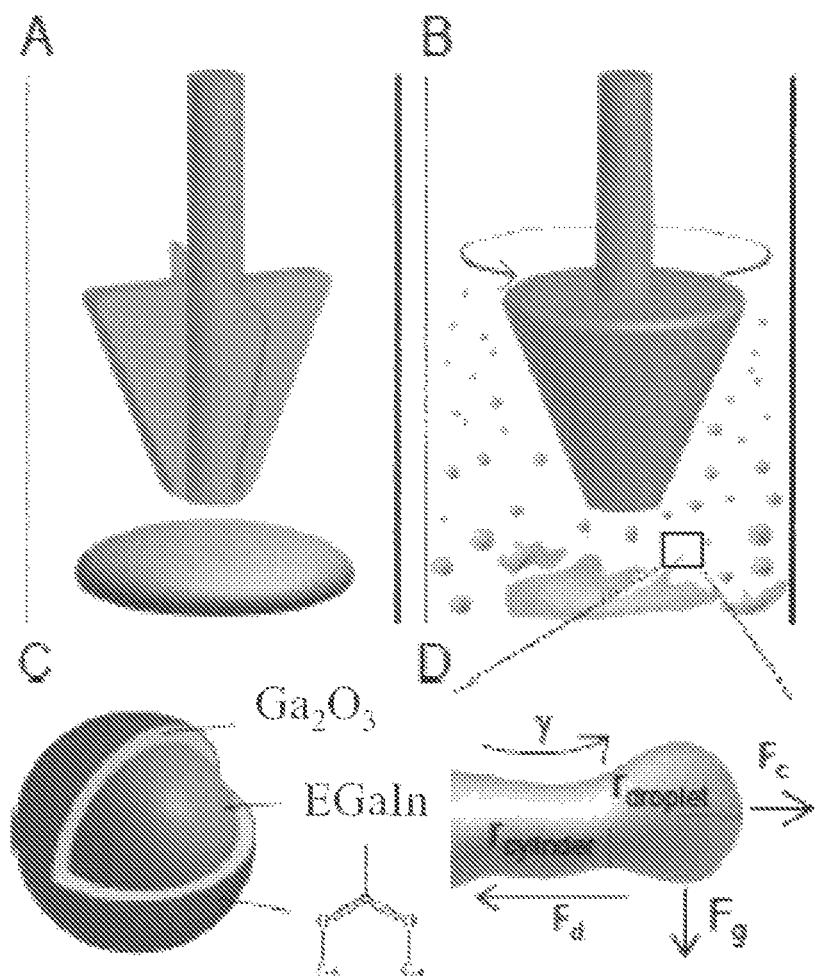
FIG. 6 is a series of schematic illustrations of a method for making core-shell particles and their resulting structure in accordance with one or more aspects of the invention.

The liquid metal may be oxidized to form an oxide shell, as shown in FIG. 6C. In certain instances the oxide is a thin and self-limiting oxide shell, but as discussed above, the thickness of the oxide layer may be increased by exposing the liquid metal to further oxidizing conditions. For example, heating the liquid metal in the presence of oxygen may increase the thickness of the metal oxide layer.

The organic material may be provided and characterized as previously discussed. According to various aspects, the organic material attaches to the surface of the oxide. For example, the liquid metal may be gallium and the organic material may be a carboxylic acid such as acetic acid. As shown in FIG. 6C, the acetate of the acetic acid binds to the gallium oxide. Thus, according to certain aspects, the metal oxide shell reacts with the organic molecules and anchors them.

In accordance with some embodiments, one or more organic materials may be added to the solution after the liquid metal and the at least one carrier fluid are combined. In accordance with other embodiments, a second organic material, different than the first organic material, may be added after the liquid metal, the at least one carrier fluid, and a first organic material are combined. In either instance, the later-added organic material may function to wrap either the inorganic or organic layer of the core-shell particle, and/or may function to grow off of an already existing organic layer.

According to at least one embodiment, the method further comprises applying mixing forces to the solution to produce a suspension comprising a plurality of core-shell particles, as shown in FIGS. 6A and 6B. In accordance with some embodiments, the mixing forces are at least one of shear forces, cavitation forces, milling forces, ultrasonic forces, laser ablation forces, atomization forces, and compressive forces. One or more of these forces may be applied by at least one device, non-limiting examples of which include high pressure homogenizers, jet stream devices, rotar-stator colloid mills, ball mills, high shear mixers, ultrasonic devices, mechanical alloying devices, laser devices, and atomization devices. For example, in accordance with some embodiments, a shearing apparatus may be operated in a turbulent state in order to impart high shearing forces to the liquid metal. According to some embodiments, the shear force creates a shear rate in a range of from about 600 s$^{-1}$ to about 3100 s$^{-1}$. For example, according to certain embodiments, the shear force creates a shear rate of about 2300 s$^{-1}$. According to another embodiment, the shear force creates a shear rate of about 3100 s$^{-1}$. As will be appreciated by one of ordinary skill in the art, the mixing forces may be of any magnitude suitable for forming the suspension of core-shell particles, as disclosed herein. Thus, the shear rate may be greater than 3100 s$^{-1}$, or less than 600 s$^{-1}$, depending on the application and materials used.

In accordance with various aspects, the mixing forces function to break up the liquid metal into smaller droplets. Under this approach, forces acting on a liquid metal droplet include: shear ($\gamma$), gravity ($F_g$), drag ($F_d$), centrifugal forces ($F_c$), and buoyancy ($F_b$, a minor contributor due to density differences), as illustrated in FIG. 6D. For a body immersed in a moving fluid, the nature and intensity of interactions vary with respect to its intrinsic properties and its position around the flowing fluidic body. Initially, at t=0, (i.e. a stationary drop in the presence of a moving fluid, as shown in FIG. 6A), $\gamma$ dominates and stretches the drop into a cylinder-like shape, characterized by period wave-like instabilities, as shown in FIG. 6D. On reaching the Rayleigh-Plateau limit (where the radius $r_{droplet} > 1.5\ r_{cylinder}$), the cylindrical liquid metal breaks into droplets, as shown in FIG. 6B. Once the droplet is formed, a combination of $F_d$, $F_c$ and $\gamma$ will ultimately split the droplet (i.e., work done on the droplet) until a final limit is attained where no more work is being done on the droplet ($\delta W=0$). At this mechanical limit, forces acting on the droplet equal the Laplace pressure (W=ΔP) and are directly proportional to the interfacial surface tension, $\gamma_{int}$, between the two liquids and the mean curvature, H, (hence size for spheres) of the droplet, as expressed below in Equation 1.

$$\Delta P = P_{droplet} - P_{fluid} = 2H\gamma_{int} \quad \text{Equation 1:}$$

where $P_{droplet}$ and $P_{fluid}$ are the pressure in the droplet and the shearing fluid respectively. As the droplet gets smaller, $F_d$ becomes a more dominant force. Drag force, which can be expressed in terms of the drag coefficient $C_d$, is proportional to the relative rate of momentum transported by the fluid, as expressed below in Equation 2.

Equation 2:
$$C_d = \frac{2F_d}{A\rho V^2}$$

where A is the cross-sectional area of the body normal to the velocity vector, V is the velocity of the fluid, and, ρ is the density of the fluid. Since compressible bodies evolve during flow to minimize their surface area (energy), it follows that control of shearing speed and felicitous choice of the shearing liquid (ΔP≈W limit) can lead to particles of different sizes and/or shapes.

According to some embodiments, the mixing forces are applied for a period of time sufficient to produce a plurality of core-shell particles comprising at least one of micro- and nano-sized particles. For instance, the mixing forces may produce a polydisperse suspension containing core-shell particles of varying dimensions that include micro- and nano-sized particles. According to one embodiment, the suspension may include core-shell particles having sizes with diameters that are from 6.4 nm to about 10 microns, although it will be appreciated by one of ordinary skill in the art that particles of smaller and larger sizes are within the scope of this disclosure. According to another example, the polydispersity index of the suspension may be in a range of from about 1.1 to about 4.0. For example, the polydispersity index may be about 2.8. This value may be decreased, for example, by increasing the amount of time that the aforementioned solution is subjected to the mixing forces. The value of the polydispersity index may also be affected by other process conditions, such as temperature. For example, if the temperature of the solution is increased, then the average size of the particle may be smaller. According to one related example, heating to 100° C. decreased the average size of the EGaIn particles from a diameter of about 1.1 microns (created at room temperature) to a diameter of about 232 nm, and the polydispersity index also decreased from a value of 2.8 to a value of 2.1. According to a further related example, EGaIn particles with an average diameter of 864 nm and a polydispersity index of 1.5 were created by heating EGaIn at elevated temperatures and keeping the solution at a pH of about 6. According to yet another example, heating to 100° C. decreased the average size of galinstan particles from a diameter of about 2 microns (created at room temperature) to a diameter of about 802 nm, but the polydispersity index increased, from a value of 2.9 to a value of 3.3.

In accordance with one or more embodiments, the general process described above outlines a basic reaction sequence that includes one or more of the following steps: oxidation of the metal, dissolution of the metal by the organic material such as an acid, binding of the organic molecule to the surface, and (optionally) release of the organic molecule from the surface. For example, by using in situ oxidation, and self-assembly on the oxide surface, stable three-layered EGaIn micro- and nano-sized core-shell particles may be produced. Thus, according to this example, EGaIn particle may be stabilized with a thin oxide layer shell in the presence of an aqueous acetic acid. Under ambient conditions, metals readily oxidize and form a protective oxide layer that may be further stabilized by modification of the oxide surface, such as through acetate. Further, post-synthesis modification allows for the possibility to create the particles, etch them in a non-binding acid, or etch them using a milling technique as discussed below, and then replace the inorganic and/or organic layers with a different inorganic and/or organic layer.

In accordance with some embodiments, the respective concentrations and amounts of the components of the solution may influence one or more aspects of the formed particles, such as their size and shape. Further, adding too little or too much of a component may hinder the formation of the particles. For instance, if too much acid is added to the solution, then no particles are formed. According to some embodiments, the solution may include an organic material that is combined with an inorganic material to form a solution of 5-10% organic material present in the inorganic material, such as 5% acetic acid in deionized water, or 10% acetic acid in deionized water. The concentration of organic material and inorganic material may be of any suitable concentration and/or ratio for forming the core-shell particles as described herein.

According to some embodiments, the mixing forces and other conditions, such as the ratio of the liquid metal, carrier fluid(s), and organic material(s) to one another, and other considerations such as the process duration, temperature, and pressure, may each be adjusted to produce particles of different sizes and shapes. For example, the process temperature may have an effect on viscosity of the metal and carrier fluid, such that an increase in temperature increases the rate of all the reactions. For instance, according to some embodiments, increasing the process temperature may increase the average size of the resulting particles. In accordance with some aspects, increasing the pressure may also increase the rate of the reactions, such as the oxidation reaction discussed above between the liquid metal and oxidizer. According to another example, when less carrier fluid is present in the solution, then the density of the liquid metal particles in the suspension increases, and as a consequence, the average diameter of the particles also increases. According to yet another example, when the amount of organic material present in the solution increases, such as the carboxylic acid, then the speed of dissolution of the metal particles by the acid also increases, and subsequently the diameter of the particles also increases.

According to a further aspect, using less acid in the solution and letting the solution age after synthesis allows for the creation of particles that are, on average, "rounder" in shape. It is believed that this is because less acid means that etching of the particles is slower and therefore there is less coalescence. In addition, this phenomenon implies that the particles as first made are not perfectly round due to the intensity of the mixing forces. Over time, the acid is believed to etch the oxide until the particles are rounder in shape. In accordance with a further aspect, adding acid later in the synthesis process also allows for the particles to be "rounder" in shape. According to yet another aspect, if acid is not added in the initial solution, the particles are smaller and have very rough surfaces.

In accordance with a further aspect, the intensity of the mixing force also has an effect on the size of the resulting particles. For example, the type and/or speed of a shearing device may cause a corresponding increase or decrease in particle size. According to one example, a shearing device with a speed of 17,700 rpm and a rotor assembly having a diameter of 42 mm creates higher shear forces and thus smaller particles than a shearing device with a slower speed of 11,600 rpm and a 13 mm diameter rotor assembly.

In accordance with some embodiments, the method further comprises removing at least a portion of the plurality of core-shell particles from the suspension. For example, particles may be separated from the suspension using any one of a number of devices and techniques known to those of ordinary skill in the art. Non-limiting examples of removal methods include settling, filtration, and centrifugation. The particles may then be further processed, depending on the desired application.

According to other embodiments, and as will be appreciated by one or ordinary skill in the art, core-shell particles may be prepared using different types of materials than those discussed above. For example, the liquid metal, the at least one carrier fluid, and the at least one organic material may be combined in the presence of a sulfide. In this instance, a metal sulfide forms a layer of inorganic material around the liquid metal. Even further, organic materials, such as those that contain thiols as a functional group, may be used to attach to the metal sulfide to form at least one organic layer of the core-shell particle. In accordance with one embodiment, a liquid metal such as NaK, which is known to react violently with water, may be combined with an inert carrier fluid (instead of water) and air may then function as the oxidizer and be used to form the layer of oxide material around the liquid metal core. Further, an organic carboxylic acid, phosphonic acid, or sulphonic acid may also be used to react with the surface of the NaK layer to form a thin layer of salt material.

According to at least one aspect, and as discussed above, the core-shell particles may undergo further surface modification post-synthesis. For example, the carboxylic acid group may function as an anchoring group, and any application-specific group may be attached on the other end of this organic molecule. For instance, a specific peptide sequence that may be used to bind to cells may be attached. In addition, functional groups may be attached that function to directly assemble the particle. According to certain embodiments, a multi-dentate ligand allows for this type of flexible functionality. This type of structure allows for a molecule with multiple binding functional groups to use one functional group to bind to the metal oxide, and leave others available for attachment and/or provide other functionalities.

Figure 8:
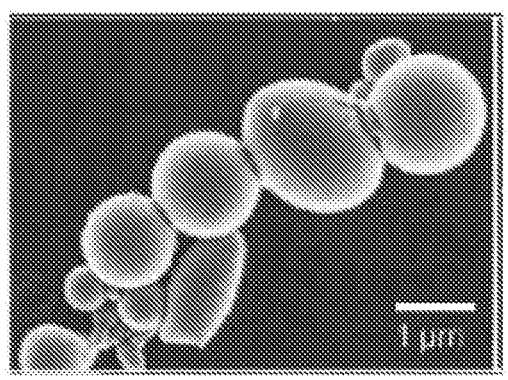
FIG. 8 is a SEM image of a chain of core-shell particles in accordance with one or more aspects of the invention.

Self-Assembly:

In accordance with one or more embodiments, two or more particles may be fused to form different shapes through capillary-driven self-assembly mechanisms. For instance, two or more particles of different shapes and sizes may be combined to form an asymmetric assembly. According to certain aspects, the core-shell particles may be self-assembled into chains (see, for example, FIG. 8) and/or hexagonally packed structures (see, for example, FIG. 9) via capillary self-assembly. Without being bound by theory, it is believed that as suspensions of the droplets dry, water pulls the particles together though capillary forces, which is strong enough to deform the particles where they touch one another to form flat regions. Further, chains may form parallel to drying fronts and hexagonally packed and cubically packed particles may be formed with flat regions forming where the individual particles meet one another.

Figure 7:
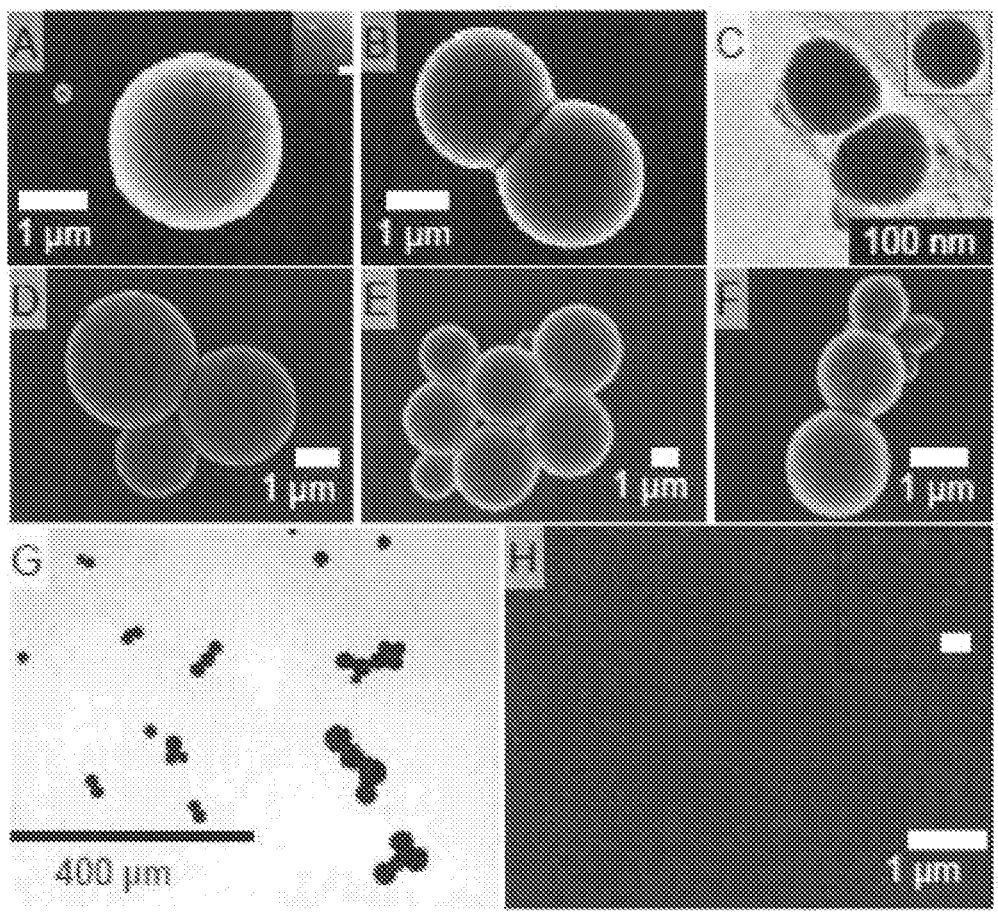
FIG. 7 is a series of images showing EGaIn particles generated using shear forces in accordance with one or more aspects of the invention.
Figure 9:
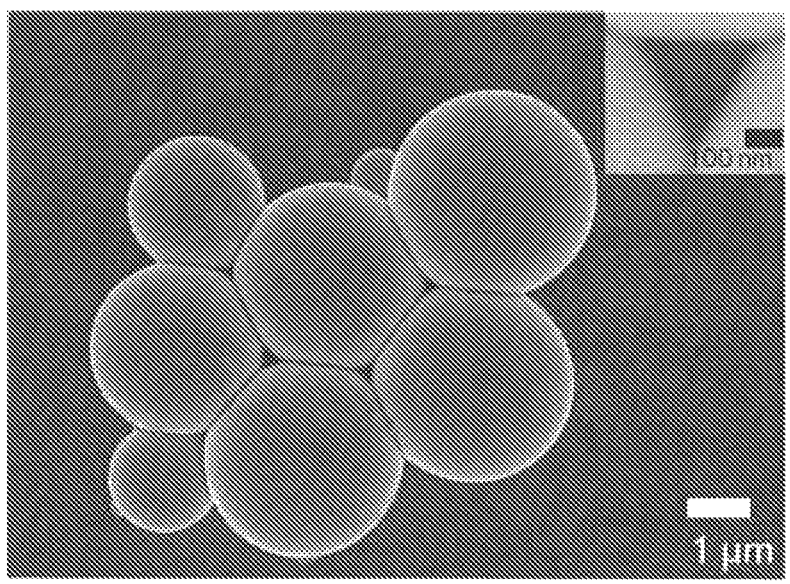
FIG. 9 is a SEM image of a group of self-assembled core-shell particles in accordance with one or more aspects of the invention.

Referring to FIG. 7, a series of images illustrate EGaIn particles generated using shear forces. FIG. 7A is a SEM image of a micro- and nano-sized particle, with smaller particles (see inset) sized at 43 and 52 nm. Capillary-driven self-assemblies of the particles give dimers, as shown in FIGS. 7B and 7C and trimer clusters, as shown in FIG. 7D, as well as other complex structures, such as those shown in FIGS. 7E-7G, FIG. 8 (illustrating a SEM image of a chain of assembled particles), and FIG. 9. For example, FIG. 9 is an enlargement of FIG. 7E and illustrates a hexagonal assembly with an equilateral triangle spacing formation (see inset) formed at the junction of three particles. Without being bound by theory, it is believed that the assemblies of particles are formed from either grouping smaller particles together, or are triggered by a larger particle formed from the coalescence of smaller particles. For example, the dimers shown in FIGS. 7B and 7C may be formed using different mechanisms. The dimer shown in FIG. 7C was determined to have a 1.2 nm gap between the particles, with the inset showing a round nanoparticle having a diameter of 85.5 nm. As discussed above, it is believed that capillary forces during the drying process may induce self-assembly, and that while these forces may be strong enough to deform the particles on contact, they are not enough to break the surface layers and cause the particles to coalesce, such as the dimer shown in FIG. 7B.

According to a further aspect, it may be possible to use the hexagonal assembly shown in FIG. 9 to create a physical mask on a surface having equilateral triangles that correspond to the junction of the three particles. Such a mask may be used in combination with a surface, such as silicon, and then removed using an acid solvent. Other uses for the core-shell particles are discussed further below.

As discussed above, the core-shell particles show one or more physical properties indicative of a malleable material. For instance, aggregated particles of micro-sized particles may appear flat on the surface where particles are in contact with one another, as illustrated in FIGS. 7B-7G, FIG. 8, and FIG. 9. According to some embodiments, this may be different from general particle aggregation because of the force pulling the particles together and deforming them into chains and into regular packing formations with flat edges where the particles make contact with one another. Thus, the flat sections provide further evidence that the particles are deformable.

Etching:

According to some aspects, the core-shell particles may fuse together if the outer oxide layer is breached or removed in some way. For instance, if the force that brings two particles together is large enough, it may break the surface oxide layer and the two liquid cores may touch and coalesce. For instance, the inorganic layer, such as an oxide, may be flexible, and the liquid metal may have a strong propensity to form spheres. When the liquid metal core of one particle is allowed to make contact with the liquid metal core of another particle, the two particles will form a larger single particle with a single spherical liquid metal core. The particles may coalesce via chemical etching of the oxide layer, such as by etching through the native oxide layer at a slow rate using a dilute acetic acid solution, although other etching methods are within the scope of this disclosure and are discussed further below.

In accordance with some embodiments, the outer layer of the core-shell particles may be etched to facilitate formation. For example, the dimer assembly shown in FIG. 7B may be formed by removing the two outer layers of two separate particles, which allows the two cores to touch and coalesce. Thus, the particles may be capable of being reconfigured post-synthesis, and when coupled with the self-assembly mechanism discussed above with respect to FIG. 7, post-synthesis modification may be capable of producing otherwise unobtainable complex structures.

Figure 10:
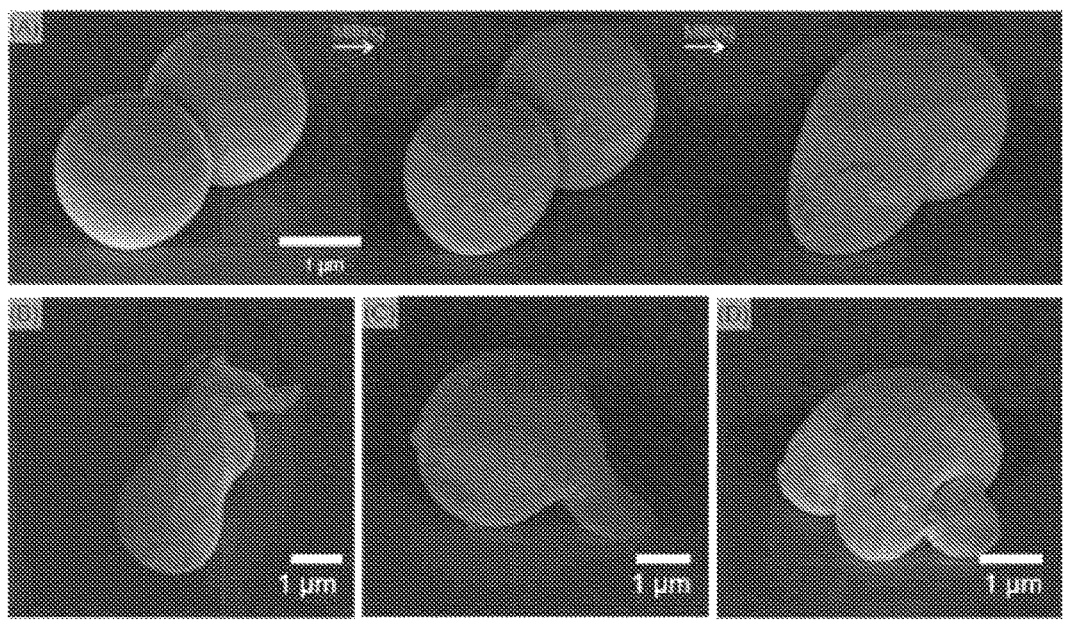
FIG. 10 is a series of SEM micrograph images showing EGaIn core-shell particles undergoing a milling process in accordance with one or more aspects of the invention.
Figure 11:
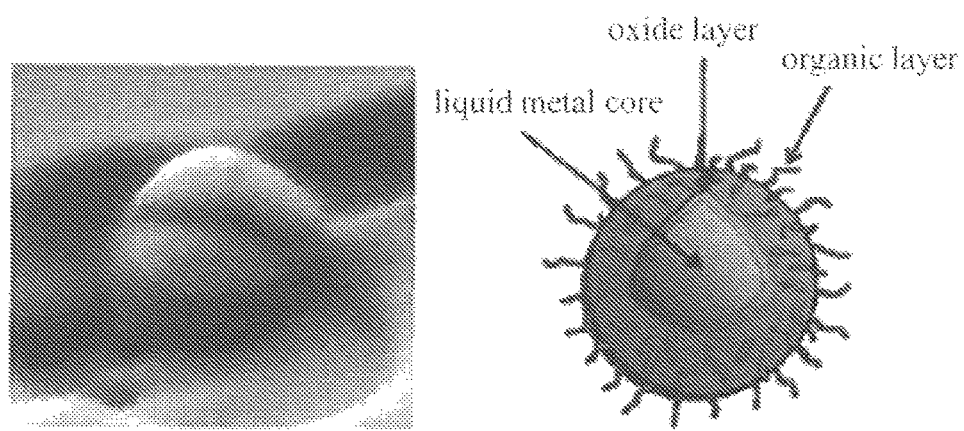
FIG. 11 is a SEM image and a schematic of an etched core-shell particle in accordance with one or more aspects of the invention.

In some embodiments, the core-shell particles may be modified by etching one or more of the inorganic and organic layers. According to certain aspects, this technique may be used to create new particles with different physical properties. In accordance with one embodiment, a focused ion beam (FIB) of gallium ions may be used to gently mill away a section of the outer surface of a core-shell particle. Using this technique, a metal ion may be accelerated in an electric field toward the particle and the resulting kinetic energy gently removes the exposed surface. For example, FIG. 10A illustrates periodic imaging by SEM of an EGaIn particle dimer etched by an FIB over a rectangular-shaped area. As shown in FIG. 10A, the initial surface of the particles has a smooth texture (FIG. 10Ai), and as the particles are milled, the top two layers (i.e., the organic and inorganic layers) are removed revealing two smooth surfaces, such as shown in FIG. 10Aii, that, upon further milling, coalesce to form one nonspherical particle, which indicates flow. This latter phenomenon is a defining property of fluids and indicates that the core of the particles is formed from the liquid metal. Without being bound by theory, it is believed that during the etch process, the surface of the oxide/organic layer that remains intact (i.e., is not being etched) functions to hold part of the liquid EGaIn in place while the exposed portion (i.e., the portion of the particle that has been etched away) of the EGaIn coalesces. FIGS. 10B-10D show other assemblies bearing particles of different sizes or shapes (inserts) that may be milled into complex structures, such as the "seahorse" formation (FIG. 10B), a "cap" formation (FIG. 10C), and a "turtle" formation (FIG. 10D). Thus, the outer layers may be etched by bombarding the particles with low energy particles to expose the underlying liquid metal core. The particles may thus be opened such as the particle illustrated in FIG. 11, with a SEM image presented on the left showing the opened particle, and a schematic presented to the right.

Uses

In accordance with one or more embodiments, the particles may be used for cancer treatment. For example, the core-shell particles may be used as in situ dosage regulators for radionuclei. The core-shell particles may be compressible and highly ductile, and therefore the amount of radiation going through these particles can be regulated by squeezing them. Hence, this reduces the amount of metal between a radionuclei and the surrounding environment and allows for dose regulation.

According to some embodiments, the particles may be used for drug delivery. For example, the organic layer can be polymerized to hold drugs and be used in drug delivery. According to some aspects, a longer chain acid may be used to prepare the particles, which may assist in time-release properties of the drug. The presence of a metal core may also allow for radio-frequency heating which may increase the flux of a drug load. This can be done using alternating magnetic fields or any RF signal generator. Biologics may also be delivered in accordance with one or more embodiments.

According to certain embodiments, the particles may be used in meta-materials. Having a smooth surface and a layer of organic material may allow for the deposition of a metal on top of the particles to make ring resonators which can be used for optical cloaking or related applications.

In accordance with some embodiments, the particles may be used in imaging. For instance, the particles can be used in plasmonics. The difference in density among the multilayers can be tuned to manipulate surface plasmons and therefore can function as surface waveguides, especially in a nanowire configuration or with a second layer of metal on them. In at least some embodiments, the particles may be used as contrast agents in applications using ultrasound.

According to various embodiments, the particles may be used in diagnostics. The organic layer may be used as an anchor for a biomarker or biologics. Since the particles are malleable, they can be used for in vivo disease monitoring or in vitro testing where the optically transparent oxide layer may allow light to pass through and reflect back from the metal surface, which may increase the intensity of a diagnostic signal in fluorescence-based (or other optic-based) applications.

In some embodiments, the particles may be used as mirror coatings. The particles may be dispersed into liquids and used to create mirror coatings on solid objects or in low concentration as scattering agents. These metal coatings may be used, for example, to block RF and aid in heat transfer.

According to various embodiments, the particles may be used in nanosolders. For example, the outer layers of the particles may be breached to release the soft metal core and the flowing liquid can be used to make electric connections.

According to some embodiments, the particles may be used as a leak detector. Blending the particles into a polymer matrix can help protect the polymer from UV damage by reflecting light away from the polymer. The particles may crack and release their contents if the polymer also cracks. This leakage may be detectable optically or electrically, since the metal may be both highly reflective and conductive.

In accordance with certain embodiments, the particles may be used in metallic inks. By coating the particles in a charged organic layer, the particles may be manipulated using an electric field. These particles may then be printed as a metallic ink. In some embodiments, a surface charge on the particles may be used in dry paints or inks.

According to at least one embodiment, the particles may be used as thermal sensors. The particles may be used as heat sensors where thermal expansion of the particles can leak out the liquid metal and result in an electrical trigger.

Figure 12:
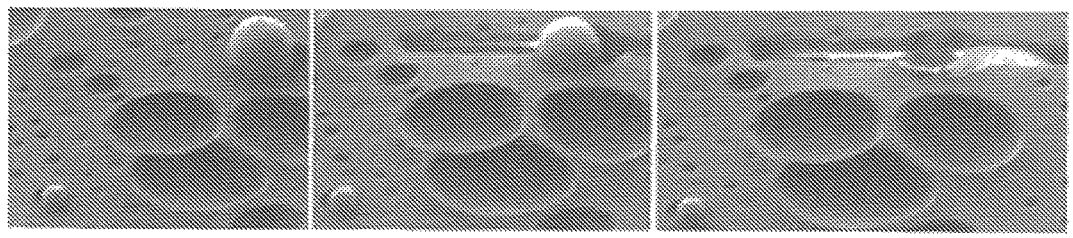
FIG. 12 is an image of an application of a core-shell particle in accordance with one or more aspects of the invention.

In some embodiments, the particles may be used to repair or solder defects in similar or different materials by breaching the outer layer of the particles and allowing the liquid metal core to fill any holes or gaps in the material. The scissioning of the particles may allow for trenches to be filled using fast ion bombardment. This technique is illustrated in the sequence of images presented in FIG. 12.

In accordance with one or more embodiments, the core-shell particles may be used to produce lines, micro-wires, nano-wires, multi-layered nanosheets, microwells, and nanowells, which may be used in microelectronic applications.

EXAMPLES

The functions and advantages of the embodiments discussed above will be more fully understood from the examples outlined below. The following examples are intended to be illustrative in nature, and are not intended to limit the scope of the disclosure.

Example 1

Particle Preparation I

A 5 mL aliquot of 5% (v/v) acetic acid (or trifluoroacetic acid (TFA)) in deionized water was placed into a flat-top glass vial having a 17 mm inner diameter and 50 mm height. A 0.6 g droplet of EGaIn was directly added to the liquid. The EGaIn was sheared using a plastic mixer with a rounded cross cross-section and a 13 mm head diameter. The plastic mixer was constructed from a Dremel™ 3000 variable speed rotary tool with an extender accessory fitted with a shearing implement. The shearing implement was a cross-shaped polytetrafluoroethylene (PTFE) structure attached to the steel rod core of the extender assembly. Rotational speeds were varied between 2,300 and 8,600 RPM. Shearing time was also varied from 5 to 30 min. The resulting suspension was allowed to sediment for 5 to 10 min and the resulting supernatant was collected, dried, and analyzed using scanning electron microscopy. The diameters of the resulting particles measured in a range of from about 18 nm to about 3.6 μm.

Example 2

Particle Preparation II

A 10 mL aliquot of 5% acetic acid in deionized water was placed into a 4 dram screw-top glass vial having a 28 mm outer diameter and 57 mm height. A 0.6 g droplet of EGaIn was directly added to the liquid. The EGaIn was sheared using the plastic mixer described above in reference to Example 1. The rotational speed used was 11,600 RPM, which corresponded to a shear rate of $3100\ s^{-1}$. Shearing time was 20 min. The resulting 2 mg/mL suspension of particles was collected, dried, and analyzed by scanning electron microscopy. The average particle size calculated from SEM images was 1.14±1.90 μm, and the diameters of the particles measured in a range of from 6.4 nm to over 10 μm in diameter. The suspension had a polydispersity index of 2.8.

Example 3

Particle Preparation III

A 75 mL aliquot of distilled white vinegar (acetic acid) was placed into a blender's 16 oz plastic cup. Approximately 1.1 g of EGaIn was directly added to the liquid in the cup. The EGaIn was sheared in the blender equipped with a variable transformer that was set at 110 V for 1 minute. The resulting suspension was collected and dried.

Example 4

Particle Composition

Using energy-dispersive X-ray spectroscopy (EDS) in a SEM operated at a 15 kV accelerating voltage, the composition of EGaIn core-shell particles prepared using the method outlined in Example 2 was determined to be 74% gallium and 26% indium, and as indicated in FIG. 15A. These results match the initial bulk metal alloy within error. At low accelerating voltages, (e.g., 3 kV), SEM and EDS analysis became more surface sensitive and the appearance of an oxygen peak in the EDS analysis was detected at 0.41 kV. This corresponds with the knowledge that EGaIn is known to quickly form a thin outer layer, which is predominantly gallium oxide ($Ga_2O_3$) upon exposure to air. Since particle synthesis occurred in the presence of air and water, the detection of a surface oxide supports the conclusion that the particles are covered in a thin layer of gallium oxide.

Figure 13:
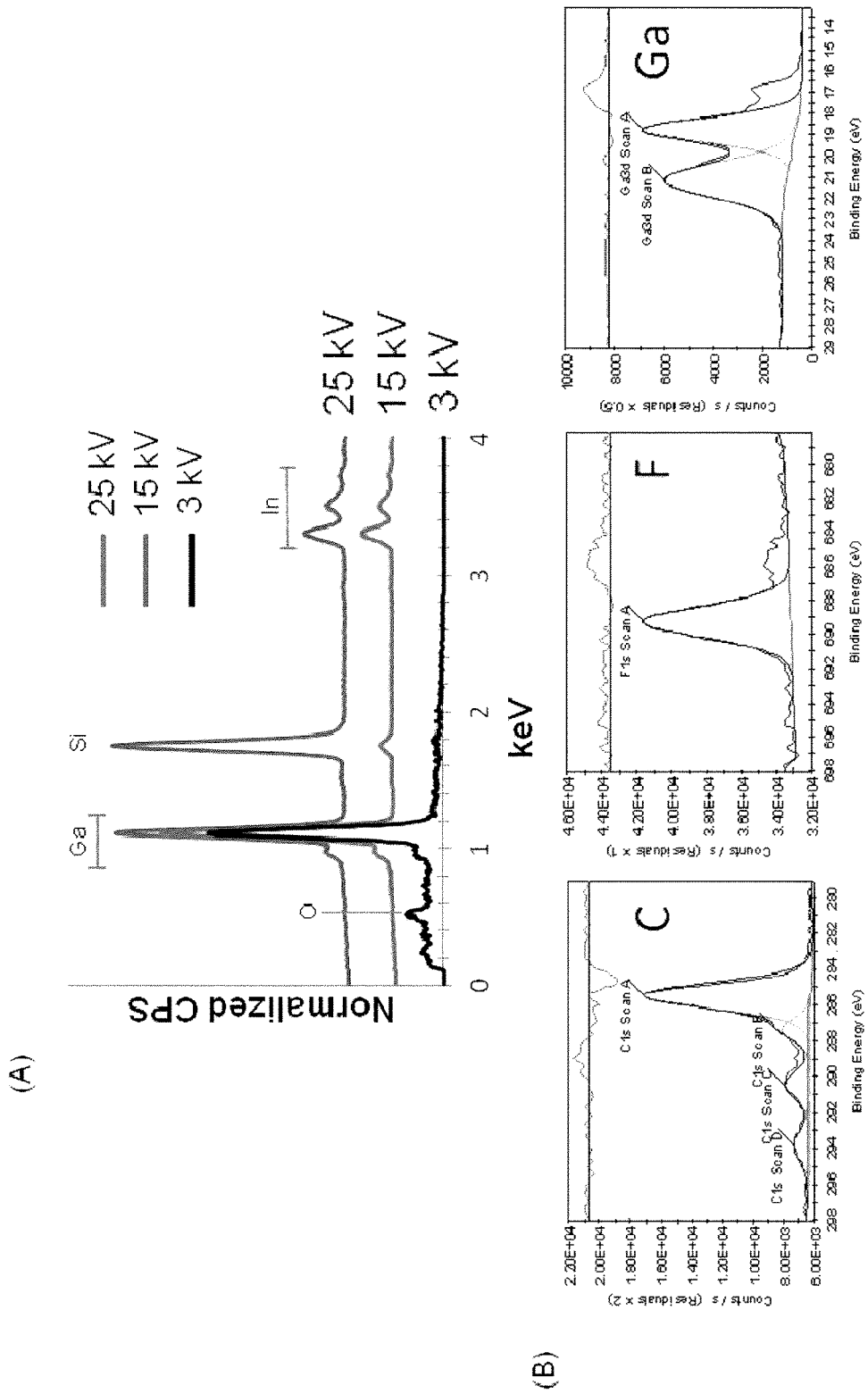
FIG. 13 illustrates EDS and XPS analysis of EGaIn particles in accordance with one or more aspects of the invention.

According to a corresponding experiment, surface characterization using X-ray photoelectron spectroscopy on bulk EGaIn (without acid) and EGaIn particles made in the presence of trifluoroacetic acid confirmed the presence of gallium oxide in both cases by the presence of a Ga 3d peak at 20.9 and 21.1 eV, respectively. This experiment included preparing EGaIn particles using TFA as described above in reference to Example 2 using 5% TFA in water. XPS analysis of the binding energy of the carbon, fluorine, and gallium are shown in FIG. 13B, and the binding energies of the elements of the control EGaIn metal and the prepared EGaIn particles are summarized below in Table 1. The results showed the presence of fluorine with a ratio of 2:2:8 non-adventitious carbon (O—C=O+CF3) to fluorine (CF3), which indicated the presence of a trifluoroacetate. Further examination of the 3d Ga oxide peaks showed a shift in binding energy from 20.88 eV in the native oxide (from the control EGaIn metal) to 21.13 eV in the prepared EGaIn particles. This increase of 0.25 eV is an indication of the interaction of the trifluoroacetate and the oxide surface, which also supports the conclusion that the TFA is binding to the EGaIn particles and also that the acetate is binding in a bridging bidentate configuration, such as that shown in FIG. 6C.

TABLE 1

Summary of XPS of EGaIn control and EGaIn made with 5% trifluoroacetic acid

| | Peak BE | Atomic % |
|---|---|---|
| EGaIn Control | | |
| Ga3d Scan A (Elemental) | 18.76 | 29.81 |
| Ga3d Scan B (Ga Native Oxide) | 20.88 | 15.99 |
| EGaIn Particles made with TFA | | |
| Ga3d Scan A (Elemental) | 18.78 | 8.18 |
| Ga3d Scan B (Ga Native Oxide) | 21.13 | 8.99 |
| C1s Scan C (O—C=O) | 290.48 | 4.12 |
| C1s Scan D (CF3) | 293.88 | 2.86 |
| F1s Scan A | 689.24 | 9.76 |

Elemental gallium was also confirmed by the presence of a Ga 3d peak at 18.8 eV for both bulk EGaIn and EGaIn particles. Further, as discussed above, acetic acid may bind to the oxide to form an outer organic layer on the particles. XPS of EGaIn particles made with TFA indicate that acetate is present and chemically binding to the surface of the particles, giving them an outer organic layer. This data indicates that at least two layers composed of acetate are bound on the oxide.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A core-shell particle, comprising:
 a liquid metal core;
 at least one layer of inorganic material surrounding the liquid metal core; and
 at least one layer of organic material attached to the at least one layer of inorganic material.

2. The core-shell particle of claim 1, wherein the liquid metal core is a metal alloy.

3. The core-shell particle of claim 1, wherein the liquid metal core has a melting point temperature less than or equal to about 40 ° C.

4. The core-shell particle of claim 1, wherein the liquid metal core comprises gallium.

5. The core-shell particle of claim 1, wherein the at least on layer of inorganic material is a metal oxide, a metal sub-oxide, or a combination of both.

6. The core-shell particle of claim 1, wherein the at least one layer of inorganic material is less than 1 nm in thickness.

7. The core-shell particle of claim 1, wherein the at least one layer of inorganic material is self-passivating.

8. The core-shell particle of claim 1, wherein the at least one layer of organic material is derived from a carboxylic acid.

9. The core-shell particle of claim 8, wherein the carboxylic acid is acetic acid.

10. The core-shell particle of claim 1, wherein the core-shell particle has a viscosity in a range of from about 0.89 cP to about 1.64 cP.

11. The core-shell particle of claim 1, wherein the core-shell particle is at least one of a micro- and nano-sized particle.

* * * * *